United States Patent
McCarthy

(10) Patent No.: US 7,126,042 B1
(45) Date of Patent: Oct. 24, 2006

(54) RECOMBINANT OLEOSINS FROM CACAO AND THEIR USE AS FLAVORING OR EMULSIFYING AGENTS

(75) Inventor: James McCarthy, Noizay (FR)

(73) Assignee: Nestec S.A., Vevey (CH)

( * ) Notice: Subject to any disclaimer, the term of this patent is extended or adjusted under 35 U.S.C. 154(b) by 660 days.

(21) Appl. No.: 10/129,720

(22) PCT Filed: Nov. 15, 2000

(86) PCT No.: PCT/EP00/11317

§ 371 (c)(1),
(2), (4) Date: Sep. 27, 2002

(87) PCT Pub. No.: WO01/36648

PCT Pub. Date: May 25, 2001

(30) Foreign Application Priority Data

Nov. 18, 1999 (EP) .................................. 99122943

(51) Int. Cl.
C12N 15/82 (2006.01)
C12N 15/29 (2006.01)
C12N 5/14 (2006.01)
C07H 21/00 (2006.01)
A61K 36/00 (2006.01)

(52) U.S. Cl. .................. 800/278; 435/468; 435/320.1; 435/419; 435/69.1; 536/23.4; 536/23.6; 530/370

(58) Field of Classification Search ................ None
See application file for complete search history.

(56) References Cited

FOREIGN PATENT DOCUMENTS

WO   WO 96/38472    5/1996

OTHER PUBLICATIONS

Hughes et al. article entitled "Cotton (*Gossypium hirsutum*) MatP6 and MatP7 Oleosin Genes" *Plant Physiol.* (1993) 101: 697-698.
Voigt et al. article entitled "In-vitro formation of cocoa-specific aroma precursors: aroma-related peptides generated from cocoa-seed protein by co-operation of an aspartic endoprotease and a carboxypeptidase" *Food Chemistry* 49 (1994) 173-180.
Voigt et al. article entitled "Cocoa-specific aroma precursors are generated by proteolytic digestion of the vicilin-like globulin of cocoa seeds" *Food Chemistry* 50 (1994) 177-184.
Huang article entitled "Oil Bodies and Oleosins in Seeds" *Annu. Rev. Plant Physiol. Plant Mol. Biol.* 1992, 43:177-200.
Leprince et al. article entitled "Oleosins prevent oil-body coalescence during seed imbibition as suggested by a low-temperature scanning electron microscope study of desiccation-tolerant and -sensitive oilseeds" *Planta* (1998) 204:109-119.

*Primary Examiner*—Ashwin Mehta
*Assistant Examiner*—Vinod Kumar
(74) *Attorney, Agent, or Firm*—Bell, Boyd & Lloyd LLC

(57) ABSTRACT

The present invention pertains to recombinant genes coding for oleosin proteins in *cacao* and to polypeptides encoded by said genes. In particular, the present invention relates to the use of such genes and gene products for the manufacture of emulsifiers, encapsulating agents, and flavor components useful in the food, pharmaceutical, and cosmetic industries.

13 Claims, 3 Drawing Sheets

Fig. 4

```
                                                                    * Majority
    Met Ala Asp Asp Asp Asn Lys His Gln Ile Gln Val His Gln His His Arg Phe Asp Gln  Majority 1  Met Ala Asp Arg Asp Arg Pro His Gln Ile Gln Val His Gln His His Arg Phe Asp Gln  16.9kDa Cacao Oleosin cDNA   SEQ ID No. 3
 1  Met Ser Asn Asp Gln Asn Lys Pro Met Thr Gln  -   -   -   -   -   -   -   -   -   15.8kDa Cacao Oleosin cDNA   SEQ ID No. 4

* Majority
    Gly Gly Lys Leu Tyr Glu Ser Ala Ser Gly Pro Ser Ala Thr Gln Ala Ala Ala Val Leu  Majority 21  Gly Gly Lys Asn Tyr Gln Ser Ala Ser Gly Pro Ser Ala Thr Gln Val Leu Ala Val Leu  16.9kDa Cacao Oleosin cDNA   SEQ ID No. 3
12   -   -  Lys Leu Tyr Glu Ser Ala  -   -  Pro Ser Ser Arg Gln Ala Ala Lys Phe Leu  15.8kDa Cacao Oleosin cDNA   SEQ ID No. 4

* Majority
    Thr Ala Leu Thr Val Gly Gly Ile Leu Leu Ala Leu Ala Gly Leu Thr Leu Thr Gly Thr  Majority 41  Thr Leu Leu Pro Val Gly Gly Ile Leu Leu Ala Leu Ala Gly Leu Thr Leu Thr Gly Thr  16.9kDa Cacao Oleosin cDNA   SEQ ID No. 3
29  Thr Ala Thr Thr Leu Gly Ala Thr Leu Leu Phe Leu Ser Gly Leu Thr Leu Thr Gly Thr  15.8kDa Cacao Oleosin cDNA   SEQ ID No. 4

* Majority
    Val Ile Gly Leu Ile Val Ala Thr Pro Leu Phe Val Ile Phe Ser Pro Val Leu Val Pro  Majority 61  Val Ile Gly Leu Cys Val Ala Thr Pro Leu Phe Ile Ile Phe Ser Pro Val Leu Val Pro  16.9kDa Cacao Oleosin cDNA   SEQ ID No. 3
49  Val Met Ala Leu Ile Met Ala Thr Pro Leu Met Val Ile Phe Ser Pro Ile Leu Val Pro  15.8kDa Cacao Oleosin cDNA   SEQ ID No. 4

* Majority
    Ala Gly Val Ala Val Gly Leu Ala Val Ala Gly Phe Leu Ser Ser Gly Gly Phe Gly Val  Majority 81  Ala Ala Ile Ala Val Gly Leu Ala Val Ala Gly Phe Leu Ser Ser Gly Ala Phe Gly Leu  16.9kDa Cacao Oleosin cDNA   SEQ ID No. 3
68  Ala Gly Val Val Ile Phe Leu Val Ile Thr Gly Phe Leu Phe Ser Gly Gly Cys Gly Val  15.8kDa Cacao Oleosin cDNA   SEQ ID No. 4

* Majority
    Ala Gly Leu Ser Ala Leu Ala Tyr Val Phe Asn Tyr Val Arg Gly Lys His Ala Thr Gly  Majority 101 Thr Gly Leu Ser Ser Leu Ala Tyr Val Phe Asn  -   -  Arg Leu Arg Arg Ala Thr Gly  16.9kDa Cacao Oleosin cDNA   SEQ ID No. 3
88  Ala Ala Ile Thr Ala Leu Ser Trp Ile Tyr Asn Tyr Val Arg Gly Lys His Pro Pro Gly  15.8kDa Cacao Oleosin cDNA   SEQ ID No. 4

* Majority
    Ala Asp Gln Leu Asp Tyr Asp Gln Ala Lys Asn Thr Leu Ala Asp Thr Ala Gly Asp Val  Majority 119 Thr Glu Gln Leu Asp Met Asp Gln Ala Lys Arg Arg Met Gln Asp Met Ala Gly Tyr Val  16.9kDa Cacao Oleosin cDNA   SEQ ID No. 3
108 Ala Asp Gln Leu Asp Tyr  -   -  Ala Arg Asn Thr Leu Ala Arg Thr Ala Arg Asp Met  15.8kDa Cacao Oleosin cDNA   SEQ ID No. 4

* Majority
    Gly Glu Lys Ala Lys Glu Val Gly Gln Lys Val Glu Gly Lys Ala Asn Glu Gly Ala Val  Majority 139 Gly Gln Lys Thr Lys Glu Val Gly Gln Lys Ile Glu Gly Lys Ala Asn Glu Gly Thr Val  16.9kDa Cacao Oleosin cDNA   SEQ ID No. 3
126 Thr Glu Lys Ala Lys Glu Tyr Gly Gln Tyr Val Gln His Lys Ala Gln Glu Val Ala Gln  15.8kDa Cacao Oleosin cDNA   SEQ ID No. 4

* Majority
    Gly Ser  -                                                      Majority 159 Arg Thr ter                                                     16.9kDa Cacao Oleosin cDNA   SEQ ID No. 3
146 Gly Ser ter                                                     15.8kDa Cacao Oleosin cDNA   SEQ ID No. 4
```

RECOMBINANT OLEOSINS FROM CACAO AND THEIR USE AS FLAVORING OR EMULSIFYING AGENTS

BACKGROUND OF THE INVENTION

This invention pertains to recombinant genes coding for oleosin proteins in *cacao* and to the polypeptides encoded by said genes. In particular, the present invention relates to the use of such genes and gene products for the manufacture of emulsions and flavor.

In a variety of different plants, such as e.g. in soybean, rapeseed or sunflower oily components that are insoluble in water, are stored in subcellular structures termed "oil bodies". The oil stored in these particles form cellular food reserves that may be mobilized quickly when large increases in cellular metabolism are required, such as during seed germination or pollen tube growth. Most plant seeds contain stored TAG's (triacylglycerols) as food reserves for germination and post germination growth, although the level of TAG's stored in seeds varies between different plants.

Intracellular oil bodies of seeds are generally between 0.5 and 2 µM in diameter (Tzen et al., Plant Physiol. 101 (1993), –276) and are considered to be composed of a matrix of TAG's surrounded by a phospholipid layer and associated with a set of different proteins, that are called oil body proteins or oleosins. The function of said oleosins is deemed to reside in the maintenance of the oil reserves of seeds and pollen in small stable droplets providing a high surface to volume ratio which facilitates the rapid conversion of the TAG's into free fatty acids via lipase mediated hydrolysis at the oil body surface.

Genomic clones encoding oleosins have been isolated for two species, namely *maize* (Browman et al., J. Biol. Chem. 265 (1987), 11275–11279) and *carrot* (Hatzopoulos et al., Plant Cell 2 (1990), 457–467). Moreover, from the cultivated oilseed *Brassica napus* cDNA clones could be obtained and the genomic organisation of the corresponding gene could be verified (Murphy et al., Biochem. Biophys. Acta 1088 (1991), 86–94). However, not any plant is presumed to make use of such oleosins and for *cacao* it was generally held that no such genes/proteins are present (Leprince et al., Planta 204 (1998), 109–119).

Most of the plant seed oil bodies and/or oleosins analyzed to date have been derived from seeds that undergo drying during maturation and can be stored safely for long periods under dry, low temperature conditions ("orthodox" seeds). To this end, genomic clones encoding oleosins have been isolated for two species, namely *maize* (Browman et al., J. Biol. Chem. 265 (1987), 11275–11279) and *carrot* (Hatzopoulos et al., Plant Cell 2 (1990), 457–467). Moreover, Murphy et al. report in Biochem. Biophys. Acta 1088 (1991), 86–94 the isolation of a cDNA clone and the genomic organisation of oleosin in the cultivated oilseed *Brassica napus*.

In addition, studies have been carried out on oleosin proteins of two other groups of seeds. Seeds that do not undergo desiccation during late maturation and are usually killed at a high water content and low temperatures (recalcitrant seeds; e.g. *cacao* and red oak) and seeds that do undergo desiccation, but are sensitive to storage at temperatures below 0° C. ("intermediate" seeds; coffee and neem) (Leprince et al. (1998) Planta 204, 109–119.). The data presented in this report lead to the conclusion that the seeds of red oak had very low levels of oleosin proteins while *cacao* did not seem to have any oleosin proteins at all. In contrast thereto, "intermediate" seeds were shown to have both oil bodies by electron microscopy and levels of oleosins similar to that observed in "orthodox" seeds, such as the rape seed *Brassica napa*.

The known oleosins turned out to be small alkaline proteins having an average weight of about 15 to 26 kDa and exhibiting an unusually long central hydrophobic region (about >70 amino acids). In an intact oil body within the cell this hydrophobic region is deemed to reside within the TAG matrix and anchor the oleosin in the oily central matrix. The N-terminal region of known oleosin proteins have been found to be rather diverse both in sequence and length.

Cacao is an important raw material for manufacturers of confectionery and other products, for e.g. chocolate. It is known that during fermentation of *cacao* the existing protease activity in the *cacao* seed results in the formation of an increased level of *cacao* flavor precursors, such as hydrophilic peptides and hydrophobic amino acids, which contribute significantly to the typical flavor the consumer knows as the *cacao* flavor (Mohr, W. W., Landschreiber, E., and Severin, T., (1976) Fett. Wissenschaft. Technologie Vol 78 88–95; Voigt, J., Biehl, B., Heinrichs, H., Kamaruddin, S., Gaim Marsoner, G., and Hugi, A. 1994 Food Chemistry 49, 173–180). This increase of flavor precursor peptides and hydrophobic amino acids is dependent on the proteolytic activity within the seed during the fermentation process and on the amount of proteins containing these precursor peptides and hydrophobic amino acids. The progress of the fermentation reaction has to be carefully monitored so that the desired *cacao* flavor precursors will be eventually obtained. Also, the raw materials have to be evaluated for flavor potential, since *cacao* seeds deficient in an appropriate amount of proteins containing flavor precursor peptides and hydrophobic amino acids will result in a fermented material deficient in *cacao* flavor precursors. Consequently, there is a need in the art to provide *cacao* raw material that constantly has a sufficient amount of *cacao* flavor precursor peptides and hydrophobic amino acids.

SUMMARY OF THE INVENTION

The problem of the present invention is therefore to provide means to enhance the flavor potential of cacao.

This problem has been solved by providing a recombinant oleosin gene of *cacao* as identified by SEQ ID No 1 and SEQ ID No 2 or variants thereof coding for functional *cacao* oleosin polypeptides.

The DNA sequence may be incorporated in a vector, preferably in a plasmid, and brought into a plant of interest to e.g. overexpress the *cacao* oleosin gene.

According to another preferred embodiment the polypeptide encoded by the recombinant oleosin gene according to this invention exhibits an amino acid sequence as identified by SEQ ID No 3 or SEQ ID No 4.

According to yet another preferred embodiment the *cacao* oleosin polypeptide may be used for preparing emulsifiers or may be used in the preparation of flavor, According to yet another preferred embodiment the present invention provides a food product containing an oleosin polypeptide and preferably enzymatically degraded products thereof.

According to another embodiment cacoa oleosin proteins or derived peptides may be used to encapsulate oil soluble molecules for example certain drugs, vitamins and various nutritional supplements.

Additional features and advantages of the present invention will be described in and apparent from the detailed description of the invention and from the figures.

BRIEF DESCRIPTION OF THE DRAWINGS

FIG. 4 shows a sequence comparison of the protein sequences SEQ ID No. 3 and SEQ ID No 4; black regions mark sequences conserved in the two protein sequences.

DETAILED DESCRIPTION OF THE INVENTION

During the extensive studies leading to the present invention the present inventors have found that contrary to the general belief (Leprince et al., supra) cacao does contain at least two different small molecular weight oleosin proteins. The oleosin proteins are synthesized in cacao seed and have a calculated molecular weight of about 16.9 kDa and 15.8 kDa, respectively.

Figure 2:
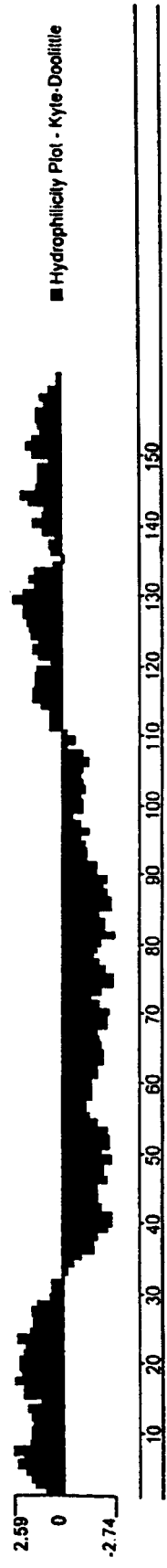
FIG. 2 shows a Kyte-Doolittle hydrophobicity plot of the 16,9 kDa cacao oleosin protein.
Figure 3:
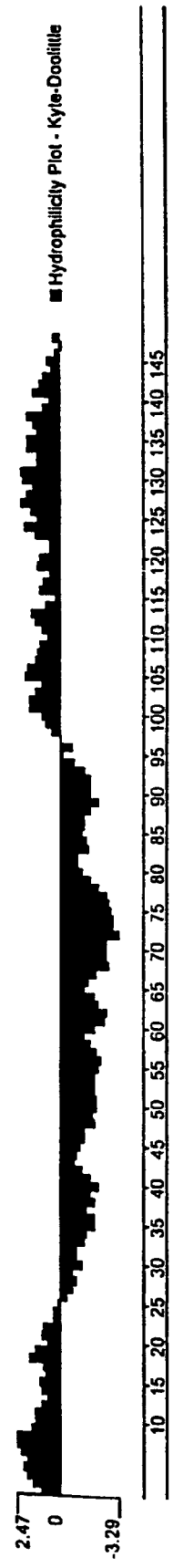
FIG. 3 shows a Kyte Doolittle hydrophobicity plot of the 15,8 kDa cacao oleosin protein.

Upon identifying the DNA sequence and the putative protein sequence the cacao oleosin proteins could be shown to contain regions of both high hydrophobicity and high hydrophilicity, as derived from a Kyte Doolittle plot (see FIG. 2 and FIG. 3). During a degradative process, such as is prevailing during the fermentation of cacao, said oleosin proteins will give rise to a number of different peptides and hydrophobic amino acids, which will contribute to an enhanced cacao flavor during the manufacture of cocoa products. The cacao oleosin genes may therefore be used for expressing or overexpressing, respectively, the gene in a suitable system thus being able to provide cacao flavor precursors.

The oleosin genes may be expressed in a variety of different ways known to the skilled person. Such, an expression cassette may be prepared harboring one or more copies of an oleosin gene according to the present invention and containing a promotor, suitable to express the gene in a given system. The promotor will be selected according to the requirements of the system, in which the oleosin gene is to be expressed.

Such systems include bacterial cells, such as e.g. E. coli, or yeast or insect cells. For each of the various expression systems appropriate vectors are known to the skilled person. The oleosin proteins produced in such systems may then be isolated from the cells or, in case the protein is secreted into the medium, from the culture medium itself.

According to a preferred embodiment the oleosin gene is expressed in a plant cell, more preferably in cacao itself. To this end one or more copies of an oleosin gene of the present invention may be introduced into the respective plant cells, which genes may be under the control of its endogenous promotor or under the control of an exogeneous promotor. Accordingly, an increased expression of oleosin in the plant cell will be possible.

In case the oleosin gene is synthesized in cacao itself said cacao may be directly used for the preparation of cacao flavor precursors with the result that less raw material will be required for obtaining the same degree of flavor precursors as compared to conventional cacao raw material.

As methods for introducing constructs, containing the oleosin gene operably linked with an appropiate promotor, into plant cells, there may be mentioned electroporation of protoplasts, use of bombardment with DNA coated particles or use of known bacterial vectors for plant transformation, such as the vectors used with the bacterium Agrobacterium tumefacians.

After the plant cells are transformed, they may then be regenerated into plants according to conventional methods such as is e.g. described in McCormick et al., Plant Cell Rep. 5 (1986), 81–84. Several generations may be grown and either pollinated with the same transformed strain or a different strain, while ensuring that the desired phenotypic trait is maintained. According to a preferred embodiment cacao trees may be eventually obtained, that exhibit a high content of oleosin proteins in their seeds that may serve as a precursor pool for flavor.

The oleosin proteins obtained as detailed above may also be used as an emulsifier or making use of their inherent properties to stabilize small oil droplets in a cacao cell, they may be used as an encapsulating agent for oil soluble molecules. As examples for the use of the cacao oleosin proteins there may be mentioned their use in the food industry for preparing standard food emulsions, such as cheese, yogurt, margarine, mayonnaise, vinaigrette, ice cream, salad dressing, baking products etc., or their use in the cosmetic industry for producing e.g. soaps, skin creams, facial creams, tooth pastes, lipstick, make up etc.

The present invention will now be described by means of examples, which are not construed to limit the same thereto.

EXAMPLE 1

Isolation of Cacao Seed Oil Bodies

For the isolation of cacao seed oil bodies, the cacao seeds used were from ripe pods of cacao variety EET 95 grown in the green house under open pollination conditions.

The procedure used was a modified version of an oil body isolation procedure developed by Millichip et al. (1996) Biochem. J. Vol. 314, 333–337). Eight mature and ungerminated EET 95 seeds were taken and their testa and radical were removed. Each seed was then chopped into small pieces with a sharp blade at room temperature and the material was immediately put into two falcon tubes on ice that each had 30 mls of grind buffer (0.1 M potassium phosphate buffer, 25 mM β-mercaptoethanol, 10 mM ascorbic acid, 0.3 M sucrose; final pH to 7.2 with KOH). The chopped seeds were then homogenized for 45 seconds on ice with an Ultra-Turrax T-25 and the larger N-18G head (Janke & Kunkel GmbH & Co KG). The homogenized material was quickly filtered through a 500 µM mesh screen keeping the filtrate on ice as much has possible. The material remaining on the screen was washed twice with 20 ml of grind buffer (supra). The filtrate was subsequently put in 4 clear polycarbonate corex tubes (30 ml) and centrifuged at 16,000 rpm (20,000 G) at 10° C. for 20 minutes. After centrifugation, the top "floating material" (oil bodies) was taken off the four tubes with a spatula to new corex tubes with fresh grinding buffer. The remaining "floating" material, which becomes suspended at the top of the supernatant during handling, was collected as well using a pipette and was transferred into fresh grinding buffer. For this first grind buffer wash, the volume was reduced to approximately 40–50 ml and put into two corex tubes. The "floating" material was resuspended by homogenization in the corex tubes on ice for 45 seconds with the Ultra Turrax (smaller head N-10G) and respun (20 minutes, 16,000 rpm, 10° C.). The top layer was again collected and transferred to a new tube as described above, which contained urea wash buffer (50 mM Tris-HCl, 9 M urea, 10 mM β-mercatoethanol, final pH 7.2). This partial urea wash mix was again resuspended by homogenization and centrifuged as in the previous wash step.

The "floating" material formed after centrifugation in the urea wash buffer was again transferred to a new corex tube with urea wash buffer at room temperature and this mix was homogenized as described above. The homogenized material was agitated at high speed at room temperature for 5 minutes, and then centrifuged for 20 minutes at 16,000 rpm, at 20° C. After this centrifugation step, the relatively clear wash solution was completely removed by pipetting from the corex tube with minimal loss of floating material and fresh urea wash solution was added to the same corex tubes. This method maximized the recovery of the oil bodies as the material binds to the tube walls and is lost if a new tube is used for each washing step. The floating material was rehomogenized, agitated for 15 minutes at room temperature and then centrifuged for 20 minutes at 16,000 rpm, at 20° C. (first 100% urea wash). This last wash step at 100% urea wash buffer was repeated three times.

Following the last washing step, the floating material that remained in the two corex tubes after removing the urea wash buffer was recovered in 10 mls of urea wash buffer plus 0.025% Triton X-100 and aliquoted to six 2 ml microcentrifuge tubes. These tubes were spun at 10,000 rpm for ten minutes and the solution below the "floating" oil bodies was removed. To remove the fat from these oil body preparations, 1 ml of acetone was added to the oil bodies in each tube. This mixture was then vortexed vigorously and then sonicated 2–4 minutes at room temperature. The tubes were then spun at room temperature for 5 minutes at 10,000 rpm. The supernatants were removed and the acetone extraction procedure was repeated 4 times. Finally, the pellets recovered were dried under vacuum in a speed-vac (SAVANT).

EXAMPLE 2

Isolation and Analysis of a Cacao Oil Body Protein by SDS-PAGE and Peptide Sequence Analysis 60 μl of SDS-PAGE gel loading buffer (62.5 mM Tris-HCl pH 6.8, 12.5% glycerol, 2% SDS, 715 mM β-mercaptoethanol, 0.025% bromophenol blue) were added to two microcentrifuge tubes containing acetone extracted oil bodies prepared as described in example 1. This material was heated to 50° C., sonicated twice for 5 minutes, vortexed, and then centrifuged. The supernatants were combined and then run in three wells of a freshly prepared 20 cm 15% SDS-PAGE gel prepared with duracryl (ESA Chelmsford, Mass. U.S.A.). After migration, the gel was fixed twice for 20 minutes in 50% methanol, 10% acetic acid, and water. The gel was stained over night with a solution of 45% methanol, 10% acetic acid, and water with 3 mg amido black per 100 ml. Then, the gel was rinsed with Milli Q purified water several times.

Figure 1:
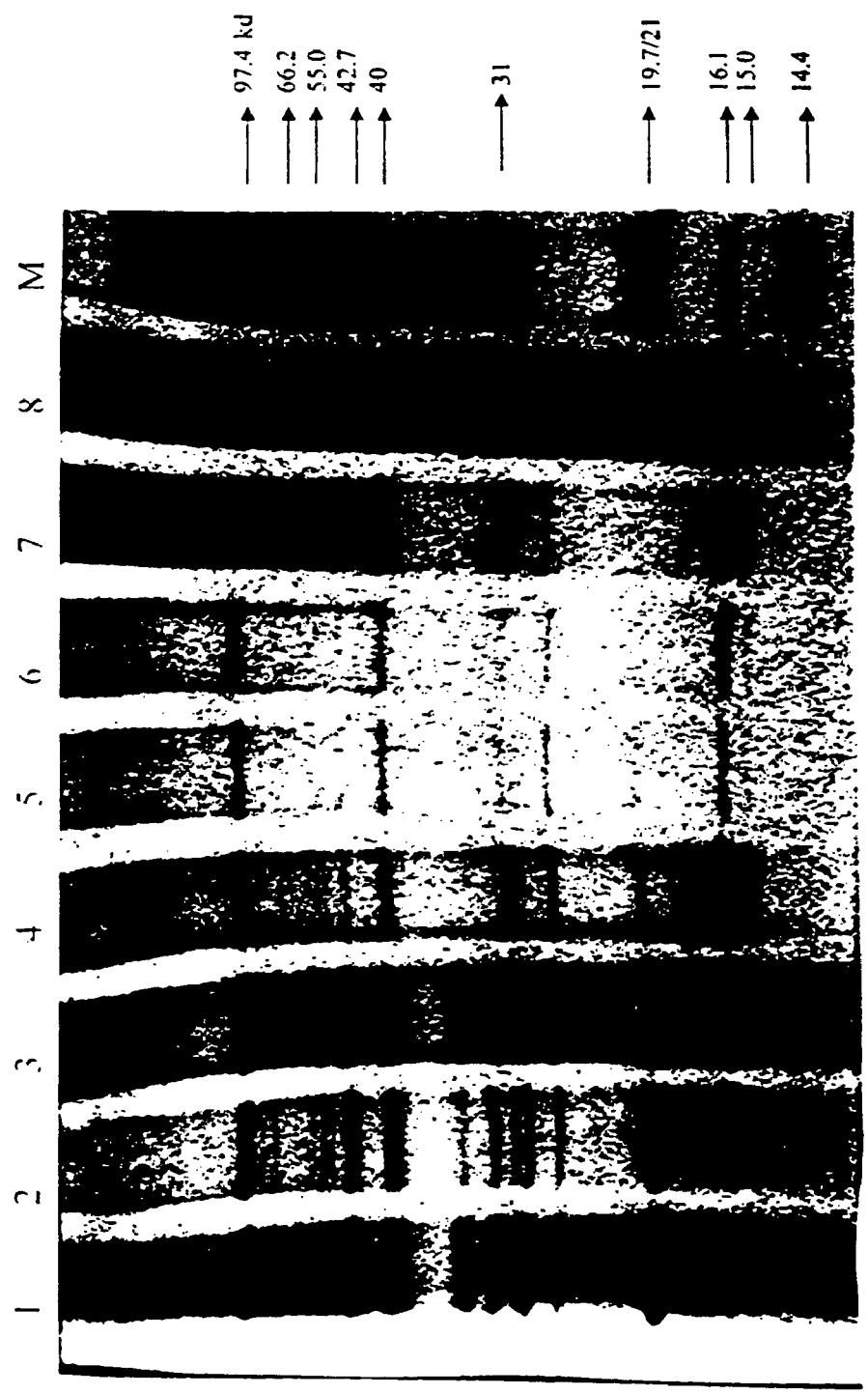
FIG. 1 shows a SDS PAGE gel of oil body purification, illustrating the protein profile of different fractions produced during the purification procedure; Aliqouts were taken at different stages of the purification of cacao seed oil bodies and run on 10–20% SDS-PAGE minigel and then silver stained. Lane 1, "floating" oil body material recovered from first centrifugation step; Lane 2, "floating" oil body material recovered from first grinding buffer wash; Lane 3, "floating" oil body material recovered from partial urea wash; Lane 4–6, "floating" oil body material recovered from urea washes #1–3; Lane 7 proteins recovered from acetone extracted oil bodies; Lane 8, same as Lane 7, but three fold more protein; M, promega mid range molecular weight protein markers.

FIG. 1 shows a picture of the stained SDS PAGE gel from which it becomes obvious that several proteins could be enriched during the oil body isolation procedure. The protein profile demonstrates that there has been a substantial enrichment of two bands around the size expected for oleosins, a major band with an apparent molecular weight of 16.1 kDa and a less intense band with an apparent molecular weight of 15.0 kDa. A larger amount of the same sample was then run on a long preparatory SDS PAGE gel. The major band at around 16.1 kDa was cut out, subjected to trypsin hydrolysis by incubating the gel slice in 200 uL Tris-HCl 0.05 M pH 8.6, 0.01% Tween 20 and 0.2 μg sequencing grade trypsin for 18 hours at 30° C. The peptides thus obtained were separated on an in-line combination DEAE-C18 HPLC column (DEAE-Aquapore, 7 um 2.1×30 mm from Perkin Elmer; C-18 column catalogue #218TP52 2.1×250 mm from VYDAC) using a gradient of 2%–45% acetonitrile in 0.1% TFA. One large peptide peak was chosen for N-terminal sequence analysis.

The peptide sequence was performed on a 494 ABI sequencer using Edman degradation chemistry according to the manufacturer, and yielded the following sequence as identified by SEQ ID NO: 5

Met Gln Asp Met Val Gly Tyr Val Gly Gln Lys Surprisingly, the sequence obtained showed a high homology to a sequence found in the 16.4 kDa oleosin of *Gossypium hirsutum* (cotton, Hughes, D. W., Wang, H. Y. and Galau, G. A. (1993) Plant Physiol. 101, 697–698), supporting the assumption that the *cacao* oil body protein investigated was indeed an oleosin protein.

EXAMPLE 3

Preparation of mRNA from Cacoa Seeds.

The mRNA used for the cDNA library construction was isolated from seeds of an immature mostly green pod of EET 95 grown in the green house under open pollination conditions. The matrix tissue encasing these seeds was solid and the seeds displayed two very distinct developmental stages. One type of seed appeared relatively mature, i.e. the seeds were purple with only small amounts of white gelatinous matrix tissue in seed folds, the other seeds were significantly less mature, with seeds having both white and pink sections and significant amounts of the gelatinous matrix material in the seed folds. For RNA isolation, small pieces of 3 of the more mature seeds and small pieces of 2 of the less mature seeds were taken as the seeds were freed from the matrix and immediately frozen in liquid nitrogen. This material was then ground to a powder in a mortar and pestle in the presence of liquid nitrogen. The liquid nitrogen+*cacao* powder was put in a 50 ml falcon tube and the liquid nitrogen was allowed to evaporate. As the powder warmed towards 0° C., 28 ml of solution A was added (14 ml 100 mM Tris-HCl pH 8+14 ml Aqua phenol (Appligene/Oncor)+0.1% hydroxyquinoline+140 μl 10% SDS,+110 μl β-mercaptoethanol). This mixture was homogenized with a glass dounce homogenizer on ice. The resulting solution was spun for 10 minutes at 8,000 rpm. The aqueous phase was recovered and was manually mixed with 7 ml phenol+7 ml chloroform/isoamyl alcohol (Ready Red, Appligene/Oncor). The extraction was then spun at 8,000 rpm for 10 minutes. After this stage great care was taken to avoid any contamination of the sample with RNAse. The aqueous phase recovered was re-extracted twice with 14 ml chloroform/isoamyl alcohol. The final aqueous phase obtained was adjusted to 0.3 M Na acetate and 2 volumes of EtOH were added. Subsequently, the tube's content was mixed and put at −20° C. for 1 hour, at −80° C. for 15 minutes, and was then spun 30 minutes at 8,000 rpm.

The nucleic acid pellet recovered was slowly resuspended in 10 ml of 100 mM Tris-HCl pH 8. Then, 3 ml of 8 M lithium chloride were added (2 M final) followed by 2 volumes of ethanol. This mixture was put 1 hour at −20° C. followed by 15 minutes at −80° C. The nucleic acid precipitate formed was recovered by centrifugation at 8,000 rpm for 30 minutes. This pellet was resuspended in 600 µl RNase free $H_2O$ and aliquoted into small samples of 200 µl which were frozen at −80° C. The purity of the isolated RNA was verified by spectral analysis at between 220 nm and 300 nm and its integrity was demonstrated by showing the integrity of the ribosomal RNA sample after running a sample on an RNA gel under the appropriate conditions.

EXAMPLE 4

Preparation of a cDNA Library from *Cacao* Seed mRNA

Poly $A^+$ RNA was prepared using an Oligotex kit (Qiagen) and total *cacao* seed RNA prepared as described in example 3. The procedure employed was as described in the instruction leaflet for 250–500 µg total RNA. In the final step, the mRNA was eluted with 25 µl preheated elution buffer, and the column was then washed with 80 µl preheated elution buffer. The eluted material was pooled, adjusted to 0.3 M Na-acetate and the RNA was precipitated by adding two volumes of ethanol at a temperature of −20° C. for one hour and −80° C. for 20 minutes. The RNA was pelleted by spinning 15 minutes at 13,000 rpm and the pellet was washed with 70% ethanol and dried under vacuum in a speed vac. The final pellet was resuspended in 10 µl of RNase free water, and the concentration of RNA present was found to be 5–10 ng/ul using Nucleic Acid "QuickSticks" (Clontech).

The synthesis of cDNA from the poly $A^+$ mRNA was carried out using a SMART PCR cDNA synthesis kit (Clontech). The method used was as described in the kit instructions. For the first strand cDNA synthesis step, 4 µl (20–40 ng) of poly $A^+$ mRNA was used and as advised in the SMART protocol, 200 units of Gibco BRL Superscript II MMLV reverse transcriptase was used. The PCR step of the SMART protocol was also set up as directed in the kit instructions, with the proviso that merely 2 µl of the first strand reaction were added. First, 18 cycles of a PCR were run, then, 35 µl was taken out of the total reaction (100 µl) and this 35 µl was subjected to a further 5 cycles of PCR.

A pool of the two PCR reactions was then prepared, 40 µl of the 18 cycle PCR reaction and 15 µl of the 23 cycle PCR reaction. 2.5 µl protease K (Boehringer Mannheim, nuclease free, 14 µg/µl) was added to this cDNA/PCR mixture and the reaction was incubated at 45° C. for one hour. After a brief spin, the reaction was stopped by heating the mixture to 90° C. for 8 minutes. The mix was then chilled on ice, and 5 µl of T4 DNA polymerase was added (3 units/µl) and the reaction was incubated at 14–16° C. for 30 minutes. Then, 25 µl of Milli Q purified water, 25 µl phenol ("Aqua phenol"), and 25 µl choloroform/isoamyl-alcohol ("Ready Red") was added. This mixture was vortexed, spun, and the top aqueous layer was taken. The phenol layer was reextracted with 50 µl of $H_2O$. The two resulting aqueous layers were then pooled and re-extracted with chloroform/isoamyl-alcohol ("Ready Red"). The DNA in aqueous layer recovered was precipitated by adding ethanol and chilling as described above. The dried DNA obtained was resuspended in TE buffer (10 mM Tris-HCl pH 8, 1 mM EDTA) and its concentration was calculated to be approximately 75 ng/µl using the "QuickSticks" from Clontech.

The cDNA was then prepared for blunt end ligation into the PCR-Script Amp SK(+) cloning vector of Stratagene. The method used was as described in the PCR-Script Amp cloning kit (Stratagene). First, the "polishing" reaction was carried out as described in the Stratagene PCR-Script Amp cloning kit using the cloned thermostable pfu DNA polymerase included in the kit. This was achieved to ensure that the cDNA were blunt ended before the ligation reaction. The DNA thus treated was subsequently purified using the Strataprep PCR purification kit (Stratagene). The DNA was eluted from the column with 50 µl of milli Q purified water, the DNA was lyophilyzed to dryness, and 6 µl of water were added. One µl of this DNA solution was used to assess the final recovery of the cDNA. Then the following ligation components of the PCR-Script Amp kit were added to the remaining 5 µl of purified cDNA in the tube in which the DNA was dried: 2 µl of pPCR-Script Amp SK(+) cloning vector (20 ng), 1 µl PCR-script 10X reaction buffer, 0.5 µl 10 mM rATP, 1 µl Sfr1 restriction enzyme (5 U/µl), and 1 µl T4 DNA ligase (4 U/µl). This mixture was incubated at room temperature for 1 hour, then heated to 65° C. for 10 minutes. Two µl of the ligated DNA were transformed into Ultra-competent cells XL-2 Blue (Stratagene) as described in the instruction manual for these cells.

EXAMPLE 5 cDNA Library Screening

The peptide sequence obtained from the gel purified oil body protein (see example 2) was used to synthesize one set of degenerate primers that correspond to two overlapping regions of the cacoa oleosin peptide sequence. The primers have the following sequences as identified by SEQ ID NO: 6 and SEQ ID NO: 7, respectively, where N is deoxy inosine:

(1) 5' NTA-NCC-NGC-CAT-NTC-NTG-CAT 3'

(2) 5' NTT-NTG-NCC-NAC-NTA-NCC-NGC-CAT 3'

Another set of degenerate primers was designed from two different regions of the 16.4 kDa cotton oleosin protein sequence. The two peptide sequences chosen were located N-terminal to the region of the 16.4 kDa cotton oleosin that has high homology to the *cocao* oleosin peptide sequence described here.

These two sets of primers were synthesized for the screening step. Different pairs of these degenerate primers were the tested with PCR amplified cDNA derived from immature seeds of *T. cacao* variety Larringa. One primer set was found to specifically amplify a fragment of approximately 300–400 bp from the *cacao* seed cDNA.

An initial screen of the cDNA library using degenerate primers indicated that the *cocao* oleosin cDNA clone was highly represented in this library. Therefore, plasmid preparations from 19 isolated transformants were screened directly with the degenerate primer set in FIG. 2, and three positive clones were selected for further study. Two clones 1cdtc-25 and 1cdtc-47 had inserts of approximately 0.850–0.950 kb and one clone 1cdtc-42 had an insert of approximately 1–1.1 kb. Clone 1cdtc-42 was chosen for further analysis by DNA sequencing. Double strand DNA sequencing showed that clone 1cdtc-42 contained a full length insert of 934 base pairs (SEQ ID No 1). The open reading frame of this insert encodes a protein with a predicted molecular weight of 16,885 daltons (SEQ ID No 3).

Analysis of the 16.9 kDa *cacao* oleosin cDNA open reading frame showed that this protein is similar to other oleosins having a very long central hydrophobic domain surrounded by hydrophilic N-terminal and C-terminal regions (FIG. 2), and that it is a very basic protein with an isoelectric point of 9.734.

Sequencing of 13 other randomly chosen cDNA clones from this cDNA library also led to the independent discovery of the 16.9 kDa *cacao* oleosin cDNA. Furthermore, during this random sequencing experiment another *cacao* oleosin sequence of 775 base pairs was found (SEQ 2). This cDNA has an open reading frame that encodes a protein with a calculated molecular weight of 15.8 kDa (SEQ ID No 4), and encodes the oil body protein with an apparent molecular weight of 15.0 kDa that is seen in FIG. 1.

The 15.8 kDa *cacao* oleosin protein sequence also has a very long central hydrophobic domain surrounded by hydrophilic N-terminal and C-terminal regions (FIG. 2), and is a very basic protein with an isoelectric point of 9.34. Comparative sequence analysis (FIG. 4) shows that the 15.8 kDa *cacao* cDNA oleosin protein sequence is quite distinct from the 16.9 kDa *cacao* oleosin protein sequence, showing only 43.4% sequence identity with between the two 5 proteins.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A recombinant DNA sequence as identified by SEQ ID NO: 1, coding for an oleosin polypeptide of cocoa.

2. A vector comprising a DNA sequence as identified by SEQ ID NO: 1 coding for an oleosin polypeptide of cocoa.

3. The vector according to claim 2, which is a plasmid.

4. An isolated polypeptide encoded by a recombinant DNA sequence as identified by SEQ ID NO: 1 coding for an oleosin polypeptide of cocoa.

5. A polypeptide according to claim 4, which is identified by SEQ ID NO: 3.

6. A cell comprising a recombinant DNA sequence as identified by SEQ ID NO: 1 coding for an oleosin polypeptide of cocoa.

7. The cell according to claim 6, which is a plant cell.

8. The cell according to claim 7, which is a *cacao* cell.

9. A plant part comprising a recombinant DNA sequence as identified by SEQ ID NO: 1 coding for an oleosin polypeptide of cocoa which is a seed.

10. A plant comprising a recombinant DNA sequence as identified by SEQ ID NO: 1 coding for an oleosin polypeptide of cocoa.

11. The plant according to claim 10, which is a *cacao* tree.

12. A method for the production of an oleosin polypeptide comprising the step of introducing and expressing in a bacterial cell or plant cell a recombinant DNA sequence as identified by SEQ ID NO: 1 coding for an oleosin polypeptide of cocoa.

13. The method of claim 12, which includes isolating the oleosin polypeptide.

* * * * *

SEQUENCE LISTING

<160> NUMBER OF SEQ ID NOS: 7

<210> SEQ ID NO 1
<211> LENGTH: 934
<212> TYPE: DNA
<213> ORGANISM: Theobroma cacao

<400> SEQUENCE: 1

```
aagcagtggt aacaacgcag agtacgcggg gacctctctt tctctctcac ttttgctgtc      60
attaacataa tcatttctgc atttgtgaaa gctcataatt taatctctac caatggctga     120
ccgtgaccgc cctcaccaga ttcaggttca ccaacatcac cgctttgacc agggtggtaa     180
gaactatcaa tccgctagtg gaccatcagc gacccaggtt ctggctgtgc ttaccctcct     240
cccagtcggt ggcattctgc ttgcgttagc agggctgacc ctcactggca ccgtcattgg     300
gctctgtgtg gccacaccac tgttcatcat cttcagcccg gttcttgtcc cagcagccat     360
tgccgttggc ttggcagtgg ctggtttctt gtcctccggg gctttcgggt tgacggggct     420
gtcctcactc gcctatgtct ttaatcgcct gaggagggcc accggtacgg agcagctgga     480
catggaccag gctaagaggc gcatgcagga catggcaggg tatgtaggac agaagactaa     540
ggaggttgga cagaagatcg agggtaaggc taatgagggt accgtaagga catgaatttg     600
ataggagggg tacctgcttg catgggagg gcaataaagt gtagtctttt tcattctcaa     660
ggtgttgtct gtgcagttgt ttgtgtatgt ctggttagcc atactagttg agagatagtg     720
ggcaatgtaa ttagactctc gtatttgctg tctgttttttg agtttaattt gttcaattcc     780
atgtatgctt tttctttatc ttaagtcagt ctctctatct cctgtgaaaa agctagtgac     840
ttccagttaa atctctcaac ccttcagctt tgaacctctt gaatatcaat cacatcatca     900
aggttcaaaa aaaaaaaaaa aaaaaaaaaa aaaa                                  934
```

<210> SEQ ID NO 2
<211> LENGTH: 775
<212> TYPE: DNA
<213> ORGANISM: Theobroma cacao

<400> SEQUENCE: 2

```
aagcagtggt aacaacgcag agtacgcggg ggcaaccgtc ttccattttc tcacttaaat      60
ttcattgcca ttttttcactg aacactatca tcagaccgag ggccgttcat catgtcgaat    120
gatcaaaaca agccgatgac tcagaagctc tatgagtcag ctccatcttc gcgccaggcg    180
gccaagtttt tgactgcaac cacactgggt gcaacgctgc tattcttgtc tgggttaacc    240
```

```
ttgaccggga cagtgatggc cctgatcatg gccacgccac tcatggtcat tttcagccca    300
attctagtcc cggctggggt agtcattttc ctggtgatta ccgggttctt gttttccggt    360
gggtgtgggg tggcggcgat cacggcgtta tcgtggatat ataattacgt gcgagggaaa    420
catccaccag gagcggatca gctggattat gcaagaaata cgcttgcgag gacggctagg    480
gacatgacgg agaaggctaa ggagtatgga caatatgtgc agcacaaggc tcaggaggtt    540
gctcaaggat cttgaataag agtgtttagc ttagggcttg gattggttg aggtctgttg    600 gttctgtaag gtggtggtgg tagtgttgtg tcttgcttgt tgttttccat catatttgca    660
tgcatacagt gtaggtcatg tgtttttggg cttagtaatt gtaacagttg ctttagtttg    720
attctctttg tggcttcgaa aatctcgttt ctccaaaaaa aaaaaaaaaa aaaaa          775
```

<210> SEQ ID NO 3
<211> LENGTH: 160
<212> TYPE: PRT
<213> ORGANISM: Theobroma cacao

<400> SEQUENCE: 3

```
Met Ala Asp Arg Asp Arg Pro His Gln Ile Gln Val His Gln His His
1               5                   10                  15

Arg Phe Asp Gln Gly Gly Lys Asn Tyr Gln Ser Ala Ser Gly Pro Ser
                20                  25                  30

Ala Thr Gln Val Leu Ala Val Leu Thr Leu Leu Pro Val Gly Gly Ile
            35                  40                  45

Leu Leu Ala Leu Ala Gly Leu Thr Leu Thr Gly Thr Val Ile Gly Leu
        50                  55                  60

Cys Val Ala Thr Pro Leu Phe Ile Ile Phe Ser Pro Val Leu Val Pro
65                  70                  75                  80

Ala Ala Ile Ala Val Gly Leu Ala Val Ala Gly Phe Leu Ser Ser Gly
                85                  90                  95

Ala Phe Gly Leu Thr Gly Leu Ser Ser Leu Ala Tyr Val Phe Asn Arg
                100                 105                 110

Leu Arg Arg Ala Thr Gly Thr Glu Gln Leu Asp Met Asp Gln Ala Lys
            115                 120                 125

Arg Arg Met Gln Asp Met Ala Gly Tyr Val Gly Gln Lys Thr Leu Glu
        130                 135                 140

Val Gly Gln Lys Ile Glu Gly Lys Ala Asn Glu Gly Thr Val Arg Thr
145                 150                 155                 160
```

<210> SEQ ID NO 4
<211> LENGTH: 147
<212> TYPE: PRT
<213> ORGANISM: Theobroma cacao

<400> SEQUENCE: 4

```
Met Ser Asn Asp Gln Asn Lys Pro Met Thr Gln Lys Leu Tyr Glu Ser
1               5                   10                  15

Ala Pro Ser Ser Arg Gln Ala Ala Lys Phe Leu Thr Ala Thr Thr Leu
                20                  25                  30

Gly Ala Thr Leu Leu Phe Leu Ser Gly Leu Thr Leu Thr Gly Thr Val
            35                  40                  45

Met Ala Leu Ile Met Ala Thr Pro Leu Met Val Ile Phe Ser Pro Ile
        50                  55                  60

Leu Val Pro Ala Gly Val Val Ile Phe Leu Val Ile Thr Gly Phe Leu
65                  70                  75                  80
```

-continued

```
Phe Ser Gly Gly Cys Gly Val Ala Ala Ile Thr Ala Leu Ser Trp Ile
                85                  90                  95

Tyr Asn Tyr Val Arg Gly Lys His Pro Pro Gly Ala Asp Gln Leu Asp
            100                 105                 110

Tyr Ala Arg Asn Thr Leu Ala Arg Thr Ala Arg Asp Met Thr Glu Lys
        115                 120                 125

Ala Lys Glu Tyr Gly Gln Tyr Val Gln His Lys Ala Gln Glu Val Ala
    130                 135                 140

Gln Gly Ser
145

<210> SEQ ID NO 5
<211> LENGTH: 11
<212> TYPE: PRT
<213> ORGANISM: cocoa

<400> SEQUENCE: 5

Met Gln Asp Met Val Gly Tyr Val Gly Gln Lys
1               5                   10

<210> SEQ ID NO 6
<211> LENGTH: 21
<212> TYPE: DNA
<213> ORGANISM: Artificial
<220> FEATURE:
<223> OTHER INFORMATION: cacoa primer
<220> FEATURE:
<221> NAME/KEY: misc_feature
<222> LOCATION: (1)..(16)
<223> OTHER INFORMATION: deoxy inosine

<400> SEQUENCE: 6
ntanccngcc atntcntgca t                                              21

<210> SEQ ID NO 7
<211> LENGTH: 24
<212> TYPE: DNA
<213> ORGANISM: Artificial
<220> FEATURE:
<223> OTHER INFORMATION: cacoa primer
<220> FEATURE:
<221> NAME/KEY: misc_feature
<222> LOCATION: (1)..(19)
<223> OTHER INFORMATION: deoxy inosine

<400> SEQUENCE: 7
nttntgnccn acntanccng ccat                                           24
```